(12) United States Patent
Wei et al.

(10) Patent No.: US 7,495,230 B2
(45) Date of Patent: Feb. 24, 2009

(54) USING A POLARON INTERACTION ZONE AS AN INTERFACE TO INTEGRATE A PLASMON LAYER AND A SEMICONDUCTOR DETECTOR

(75) Inventors: David T. Wei, Malibu, CA (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 360 days.

(21) Appl. No.: 11/205,781

(22) Filed: Aug. 16, 2005

(65) Prior Publication Data

US 2006/0170926 A1 Aug. 3, 2006

Related U.S. Application Data

(60) Provisional application No. 60/602,117, filed on Aug. 17, 2004, provisional application No. 60/602,061, filed on Aug. 17, 2004.

(51) Int. Cl.
  *G01K 1/08* (2006.01)
(52) U.S. Cl. ............ 250/397; 250/492.2; 356/445
(58) Field of Classification Search .......... 356/445
  See application file for complete search history.

(56) References Cited

U.S. PATENT DOCUMENTS 4,460,880 A * 7/1984 Turner .................. 333/238
4,482,779 A   11/1984 Anderson ............... 136/255
5,451,980 A   9/1995 Simon et al. ............ 345/88
7,173,275 B2 * 2/2007 Estes et al. ............ 257/29
2003/0107741 A1 * 6/2003 Pyo et al. ............... 356/445
2003/0206708 A1 * 11/2003 Estes et al. ............. 385/130
2006/0170926 A1   8/2006 Wei et al. ............... 356/445

OTHER PUBLICATIONS

Ditlbacher, H., et al., "Efficiency of local light-plasmon coupling", *Applied Physics letters, AIP, American Institute of Physics*, vol. 83, No. 18, p. 3665 lefthand column, paragraph 3, p. 3667, lefthand column, paragraph 1, figures 1,3.

Jasperson, S.N., et al., "Photon-surface-plasmon coupling in thick Ag foils", *Physical Review USA*, vol. 188, No. 2, pp. 759-770 (Dec. 1969).

* cited by examiner

*Primary Examiner*—Gregory J Toatley, Jr.
*Assistant Examiner*—Tara S Pajoohi
(74) *Attorney, Agent, or Firm*—Steinfl & Bruno

(57) ABSTRACT

An integrated plasmon detector includes a top layer of material adapted to generate a plasmon when excited by a beam of light incident onto a surface of the top layer, an interface layer joined to the top layer opposite from the surface of the top layer and adapted to slow polarons emitted by the plasmon to thermal electrons, and a collector layer joined to the interface layer opposite from the top layer and adapted to collect the thermal electrons from the interface layer.

7 Claims, 3 Drawing Sheets

USING A POLARON INTERACTION ZONE AS AN INTERFACE TO INTEGRATE A PLASMON LAYER AND A SEMICONDUCTOR DETECTOR

CROSS-REFERENCE TO RELATED APPLICATIONS

This application claims the benefit of U.S. provisional Patent Application Ser. No. 60/602,117, filed Aug. 17, 2004 for "Using a Polaron Interaction Zone as an Interface to Integrate a Surface Plasmon Layer and a Semiconductor Detector" and U.S. provisional Patent Application Ser. No. 60/602,061, filed Aug. 17, 2004 for "Utilizing an Integrated Plasmon Detector to Measure a Metal Deposit Roughness on a Semiconductor Surface," both by David T. Wei and Axel Scherer, the disclosures of which are incorporated in their entirety herein by reference thereto. This application is filed on the same day as U.S. patent application Ser. No. 11/205,782, now U.S. Pat. No. 7,297,966, for "Utilizing an Integrated Plasmon Detector to Measure a Metal Deposit Roughness on a Semiconductor Surface", also incorporated herein by reference in its entirety.

STATEMENT REGARDING FEDERALLY SPONSORED RESEARCH OR DEVELOPMENT

The present invention was supported in part by grant no. F49620-03-1-0418 from the United States Air Force Office of Scientific Research. The U.S. Government may have rights in any patent issuing on this application.

BACKGROUND

1. Field

The present disclosure relates to integrated plasmon detectors.

2. Related Art

When a species of atoms (whether gas, liquid, or solid) is ionized into an equal number of free electrons and ionized atomic cores known as ions, the atoms are said to be in a plasma state. In an ideal undisturbed gaseous plasma, the density of free electrons is equal to that of the positively charged ions and the overall distribution of charge is equal, and thus neutral, throughout the plasma. When this distribution is disturbed, the electrons seek to restore their neutral positions through the combined effect of repulsion from other electrons and attraction from the uniform positive charge background of the ions. This will induce an oscillation in the electrons as they attempt to return to their neutral positions known as plasma oscillation. [The Feynman Lectures of Physics, R. P. Feynman et al., Addison Wesley, Reading, Mass. 1964, the entire contents of which are incorporated herein by reference.]

In a metal, the density of free electrons is much higher, and their temperature much lower, than in a gaseous plasma. These free electrons are thus a quantum gas and, when oscillating, form what is termed a plasmon. Free electrons oscillating at a common frequency are oscillating at plasmon frequencies that are generally very high, having a typical value on the order of $3 \times 10^{15}$ Hz (corresponding to a charge of about 12 eV). [Elementary Excitation in Solids, D. Pines, Benjamin, N.Y. 1964; and Statistical Mechanics, R. P. Feynman, Addison Wesley, Reading, Mass. 1972; the entire contents of both of which are incorporated herein by reference.] For purposes of discussion and with reference to FIG. 1(a), whereas a plasmon is understood herein to refer to the state of quantum plasma in a solid, a jellium 2 is understood to mean a quasiparticle consisting of a negatively charged core 4 shielded by positive charges 6 gathered from the surrounding ions within a Fermi-Thomas radius $\lambda_{FT}$, which is comparable to the radius of a host atom in a metal lattice. The electron thus oscillates within this atom-sized sphere of positively-charge volume, evincing a high frequency and thus displacement that is small relative to the size of the sphere. When all such electrons oscillate in phase with one another, a standing plasmon wave arises (k=0), whereas a linear series of electrons having a definite phase relationship to one another correspond to a traveling plasmon wave having definite direction and mode numbers k (k≠0).

A quantum plasma in a solid also contains individual "hot" electrons that tend to interact (i.e. collide) with each other and with jelliums much more frequently that with the host ion lattice. When a hot electron 4' penetrates a jellium 2, as shown in FIG. 1(b), there are two negative electron charges 4, 4' inside a volume 6 of a unit of positive charge. This imbalance of charge leads the jellium to disintegrate by the expulsion of both electrons such that total momentum is conserved. Conversely, when two such hot electrons collide, as shown in FIG. 1(c), the result is a stationary jellium 2 at the point of impact and one free electron 4'. Molecular physics teaches us that the probabilities of these two opposite processes are equal.

When a metal is impinged upon by a laser pulse beam having a frequency below the plasmon frequency of the metal, electrons begin to be set in motion at randomly distributed frequencies lying between the laser beam and the plasmon frequencies (between $10^{15}$ and $3 \times 10^{15}$ Hz). Initially most of these electrons are free hot electrons, with few jelliums. These hot electrons tend to favor the creation of jelliums through their collisions, and thus the subgroup of collective electron plasmonic oscillations begins to build up in jelliums as energy is transferred from the laser beam to the plasmon system. Depending on the length of the laser pulse and the thickness of the metal, the plasmon oscillations may reach a peak maximum range, with free electron density as high as $10^{23}/cm^3$. These collective oscillations have a natural frequency or plasma frequency determined by the density of electrons in the neutral distribution $n_0$, and can be expressed as $$f = \left(\frac{1}{2\pi}\right)\sqrt{\frac{e^2 n_0}{\varepsilon_0 m_e}} \qquad (1)$$

where e is the unit electron charge, $n_0$ is the neutral density of electrons in a plasma, $\varepsilon_0$ is the permittivity of vacuum, and $m_e$ is the unit electron mass.

When the laser beam ceases to impinge onto the metal, most jelliums continue to oscillate at their respective plasmon frequency characteristic of concentration and movement (mood number). When a jellium falls out of step with the whole class collective modes of existing plasmon oscillations, it drops out and an 'individual' hot electron (as opposite to a 'collective class' hot electron) results that eventually cools down to room temperature to become a thermal electron. However, if it does not pass through an adaptor layer to cool down quickly, the remaining heat will make detecting it functionally difficult.

Currently known methods and devices for measuring the decay of a plasmon all rely on photodetectors of various types to detect the emitted decay photons. This approach is limited by the fact that the decay photons have to travel a relatively long path from the surface to the detector, a path over which they undergo angular spreading misalignment, and environment influences. Thus, collection and detection of decay photons as a means of studying plasmon effects can be difficult and prone to inaccuracies. The present disclosure addresses these difficulties with a novel approach to plasmon detection: monitoring the hot electrons internally created by plasmon decay.

SUMMARY

According to one embodiment described herein, a plasmon detector comprises a top layer of material with a surface adapted to generate a plasmon when excited by an incident beam of light; an interface layer joined to the top layer opposite from the surface of the top layer and adapted to slow polarons emitted by the plasmon to thermal electrons; and a collector layer joined to the interface layer opposite from the top layer and adapted to collect the thermal electrons from the interface layer.

According to another embodiment described herein, a method for detecting a plasmon comprises selecting a top layer of material with a surface adapted to generate a plasmon when excited by an incident beam of light; joining an interface layer to the top layer opposite from the surface of the top layer, the interface layer adapted to slow polarons emitted by the plasmon to thermal electrons; joining a collector layer to the interface layer opposite from the top layer, the collector layer adapted to collect the thermal electrons from the interface layer; impinging a beam of light onto the surface of the top layer; and detecting the thermal electrons collected in the collector layer.

In further embodiments, the interface layer may comprise a substantially non-conductive n region, and the interface layer may comprise any one or more of the group comprised of ZnSe, GaP, GaAs, and Si. In yet further embodiments, the collector layer may comprise a semiconductor, and the top layer may comprises any one or more of the group comprised of Au and Ag. In a still further embodiment, an electric circuit may be connected between the collector layer and the top layer to conduct thermal electrons collected in the collector layer to the top layer.

According to a still further embodiment described herein, a method for detecting a plasmon comprises impinging a beam of light onto the surface of a metal to generate a plasmon that decays through Raman scattering photons and emitted electrons, and counting the emitted electrons.

In another embodiment described herein, a plasmon detector comprises means for generating a plasmon on a metal; means for reducing the energy of electrons emitted by decay of the plasmon; and means for counting the reduced energy electrons.

In still another embodiment described herein, a method for detecting a plasmon comprises impinging photons onto a first material to generate a plasmon that decays through Raman scattering photons and free electrons having a first energy state; causing the free electrons to form polarons in a second material and slow down to thermal electrons having a second energy state through the emission of phonons; and counting the thermal electrons.

DESCRIPTION OF THE PREFERRED EMBODIMENTS

Figure 1A:
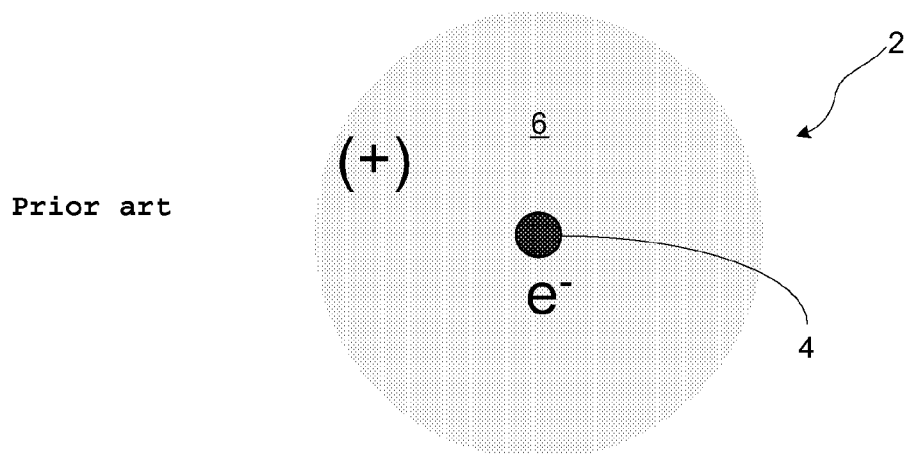
FIGS. 1(a)-1(c) are diagram representation of a jellium particle, and the formation and destruction mechanisms for a jellium particle.
Figure 1B:
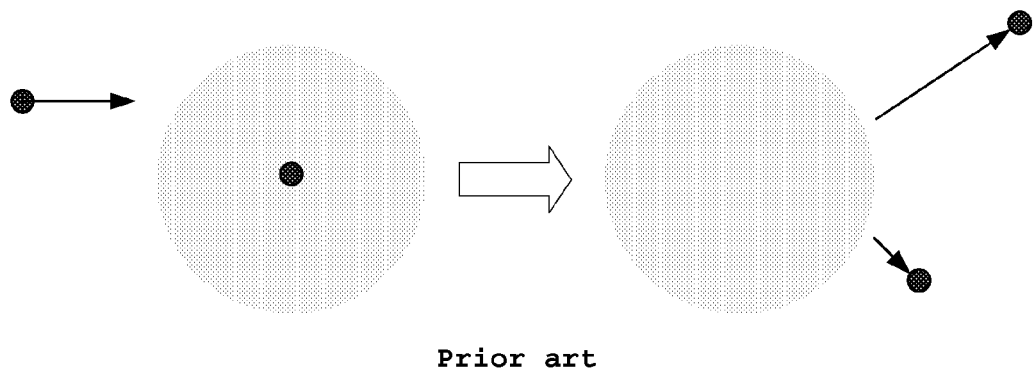
Figure 1C:
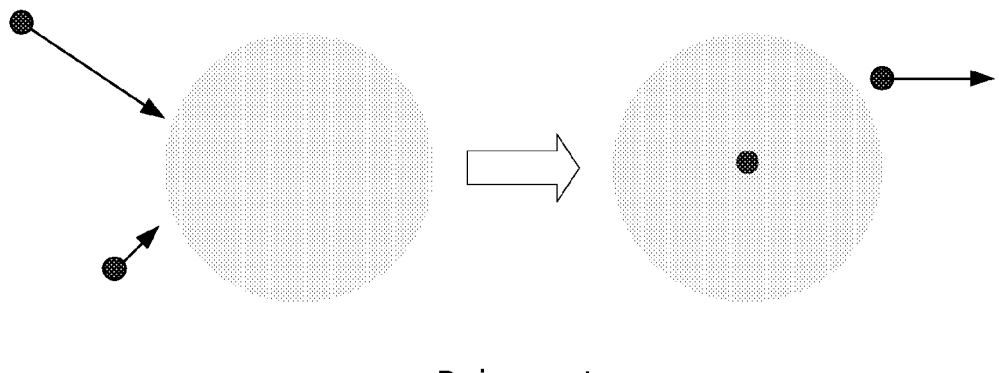
Figure 2:
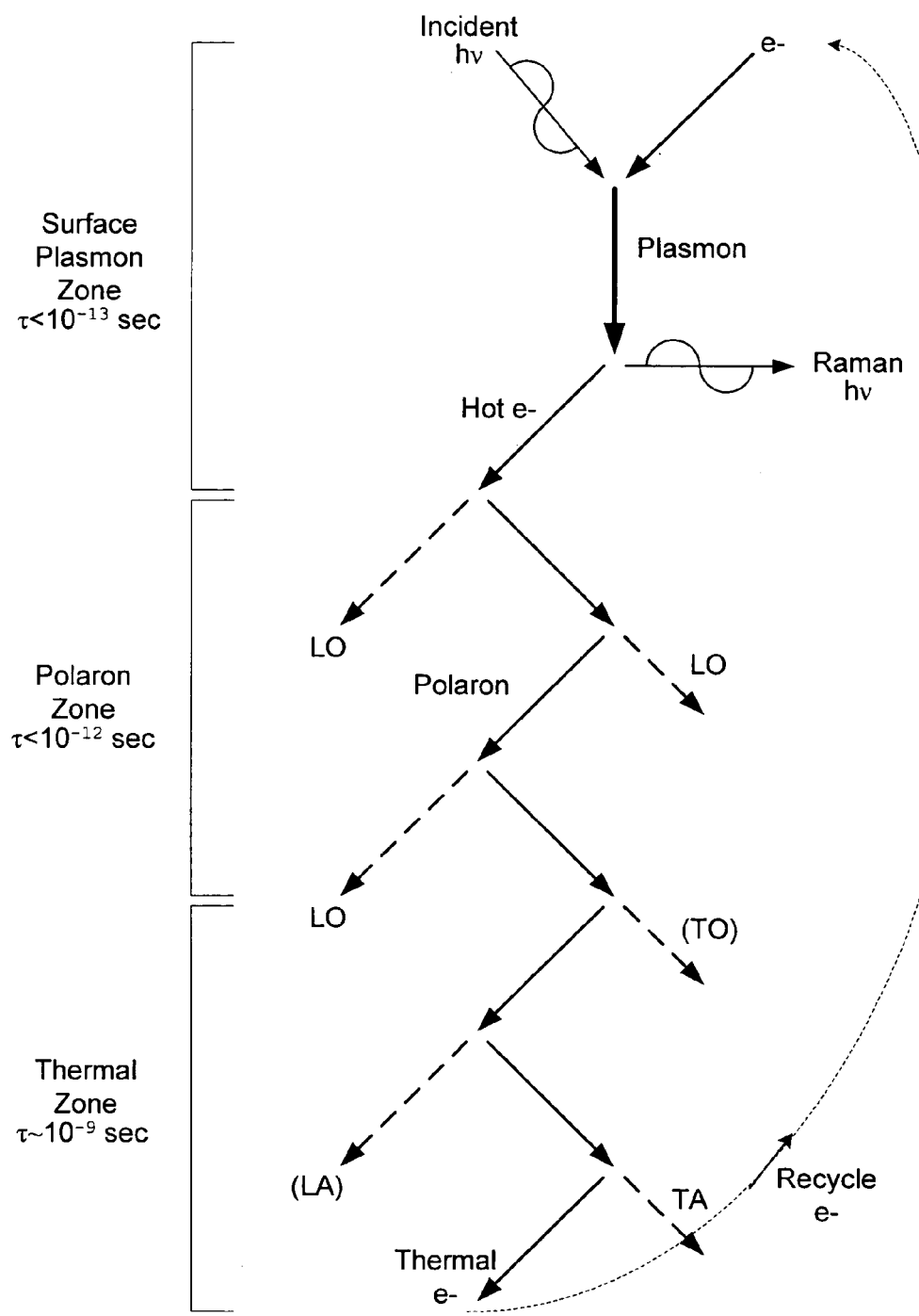
FIG. 2 is a Feynman diagram representation of a polaron decay scheme employed in embodiments described in the present disclosure.

Referring to FIG. 2, a Feynman diagram depicts the decays scheme of a jellium or plasmon particle. An incident photon laser pulse that strikes a conductive mass of material (such as silver, gold, or other metal) excites free electrons to set up a plasmon, which then decays by emitting a high-energy electron and a Raman scattering photon that is reflected back from the mass. Thus, conservation of momentum dictates that the matching high-energy electron travels in a generally opposite direction from that of the Raman photon, and away from the surface. As the plasmon decays after the pulse, and accumulation underneath the surface of such high-energy "hot" electrons of energy between 0.04 eV and 12 eV begins to collapse towards the interior of the conductive material and proceed to interact with the ionic lattice atoms of this material. If this material is polar (that is, strongly ionic in nature), these high-energy electrons are quickly quenched. This stream of high-energy electrons traveling at high velocity through such a polar lattice has a distortion affect upon the lattice that takes the form of a wave (similar, on a broad conceptual level, to a breeze flowing through a grass field). As each high-energy electron moves through the atomic lattice, it drags the lattice disturbance with it and interacts with the ionic charges in the lattice, thereby forming a new composite particle known as a polaron.

More specifically, polarons are formed by the charge coupling of a high-energy electron with the ionic charges from the solid atomic lattice, taking the form of a hot and heavy composite particle, or eigenstate, moving through the lattice. Through the charge coupling between the hot electron and the lattice ions, the electron sheds its kinetic energy to the ionic lattice one quantum per each interaction. Each such quantum of energy imparted to the lattice causes the lattice to vibrate in unison, thereby giving rise to a "wake" behind the high-energy electron. Each quantum of such lattice vibration is known as a phonon, and a high-energy electron dragging a wake of phonons behind it forms a polaron. As each phonon breaks away from the polaron, the polaron loses a quantum of energy and recoils at a random angle until it eventually loses all of its kinetic energy and becomes a "cold," or thermal, electron (having energies on the order of 0.04 eV, or room temperature). ["Oscillatory and Excitation Spectra of CdS and ZnSe," Proc. $3^{rd}$. Int. Conf. On Photoconductivity, D. T.Y. Wei et al., pp. 343-350, edited by E. M. Pell, Pergamon, N.Y., 1973, the entire contents of which are incorporated herein by reference.]

With continued reference to FIG. 2, there are four basic types of phonons, as defined in Table I below.

TABLE I

| Wave Polarization Direction/Displacement of Ions in Unit Cell | Longitudinal | Transverse |
|---|---|---|
| Along each other (Acoustic) | LA | TA |
| Opposite (Optical) | LO | TO |

The relative electron coupling strength of each of the above four types of phonons depends on the band structure and how polar the host material is (increasing across the Group IV, III-V, and II-VI sequence of semiconductors). For most popular optical crystals, the shortest emission time is for LO phonons (about $10^{-13}$ sec) and the longest emission time is for TA phonons (>$10^{-9}$ sec). The emission of any one of the four types of phonons is possible, but the ones with the shortest interaction times are favored, and the natural priority in typical semiconductors is therefore LO, TO, LA, TA. In the plasmon decay curve, LO phonon emission characterizes the initial sharp drop and TA phonon collision accounts for the slow tailing off. LA and TO phonon emissions are not important with respect to characterizing this curve.

Figure 3:
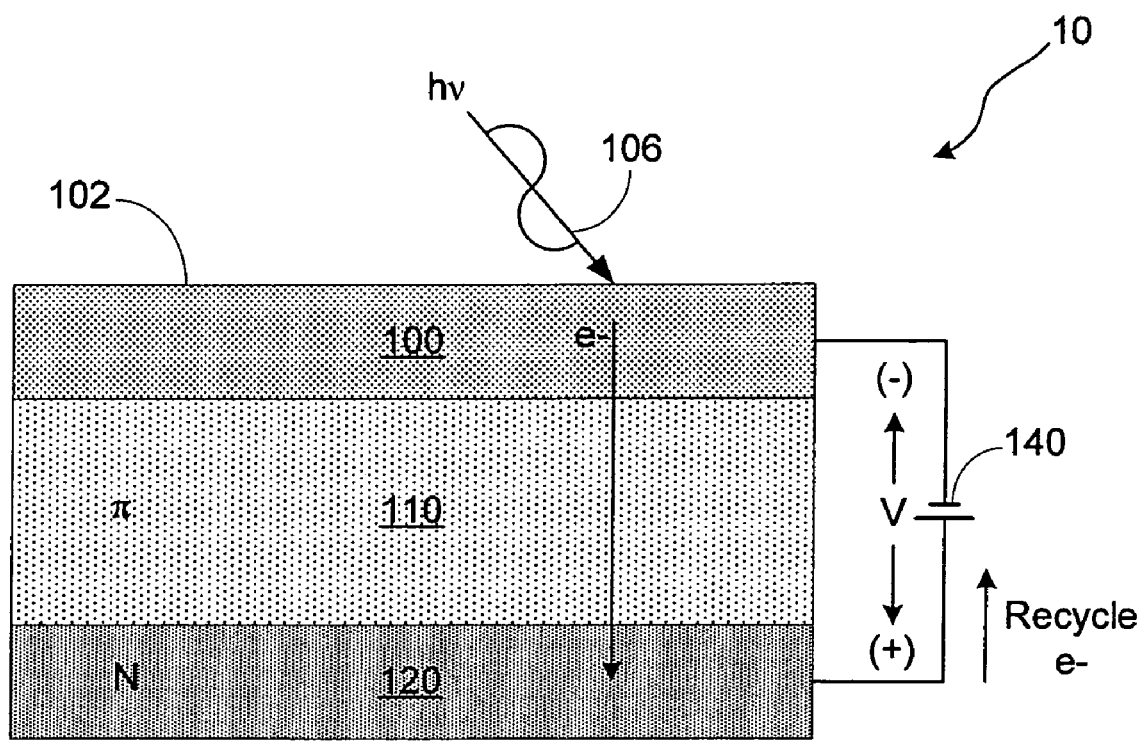
FIG. 3 is a functional block diagram, not drawn to scale, of a detector according to the present disclosure.

With reference now to FIG. 3, the present disclosure addresses solutions to the problems encountered by conventional plasmon detectors by detecting the high-energy electrons produced by the decay of the plasmon instead of the Raman photons. Thus, with continued reference to FIG. 3, one embodiment of a detector 10 according to the present disclosure includes a "plasmon" layer 100 of metal with an exposed surface 102 upon which a laser beam 106 may impinge. The metal layer 100 is selected to give rise to a plasmon when excited by a laser beam, and thus preferred materials include, among others, gold (Au) and silver (Ag).

Joined to the plasmon layer of material 100 and generally opposite from the exposed surface 102 is a "polaron" layer 110 that is selected to slow the high-energy electrons emitted by the decay of the plasmon to thermal electrons through the generation of polarons. The polaron layer 110 is most preferably a so-called pi (π) region, that is, an electric insulator substantially void of conducting host electrons or holes. Thermal electrons cannot travel across this region by drift (also called ohmic conduction), but the high-energy decay electrons can traverse such a region as polarons by diffusion, due to their high momentum concentration gradient and the random nature of polaron movements. Materials suitable for use in the polaron layer include, among others, ZnSe, GaP, GaAs, and Si. Assuming an average polaron velocity of $10^6$ m/sec, the thickness of the polaron layer 110 would typically need to be about 1 μm for LO phonon emission. The choice of materials will be dictated by, among others, the type of phonons emitted, the energy of the decay electrons, and the purity and perfection of the crystals used.

With continued reference to FIG. 3, an electrically conductive "collector" layer 120 is joined to the polaron layer 110 opposite from the plasmon layer 100. As polarons are slowed down in the polaron layer 110, the resulting thermal electrons arrive to be collected in the collector layer 120, where they can be detected and the initial incident laser beam 106 can thus be quantified. A practical material for the collector layer is a semiconductor substrate, which can be either homo or hetero junction. The thermal, or "cold" electrons that arrive in the conductive layer 120 can thus be counted in any manner known to those skilled in the art and may further be "recycled" through an external circuit 140 that sends them back to the plasmon layer 100 to form new plasmons and decay in the next cycle of plasmon decay. It is understood that the individual thermal electrons in this flow do not need to be counted, as the response of a detector measuring the thermal electron flow or current, and particularly the decay shape following each laser pulse, can provide all the information desired.

It will be appreciated by the skilled reader that the present disclosure is directed to a novel method and device for detecting and quantifying plasmons that avoid the problems found in current state of the art methods and devices. The presently disclosed embodiments detect the plasmon decay electron instead of the Raman photon and, through the provision of an interface region that slows such decay electrons to thermal levels through the generation of polarons, provide for an integrated device that unites the plasmon generation layer with the thermal electron collector layer. The thermal electrons collected in the collector can then be detected and measured with conventional electronics, and may be recycled back to the plasmon conductive layer to give rise to a subsequent plasmon and the attendant generation of decaying polarons.

While several illustrative embodiments of the invention have been shown and described, numerous variations and alternative embodiments will occur to those skilled in the art. The relative thicknesses of the various layers in FIG. 3, for instance, are not to be understood as disclosing a preferred or necessary thickness ratio among these layers. Such variations and alternative embodiments are contemplated, and can be made without departing from the scope of the invention as defined in the appended claims.

What is claimed is:

1. A plasmon detector, comprising:
   a top layer of material adapted to generate a plasmon when excited by an incident beam of light;
   an interface layer joined to the top layer opposite from the surface of the top layer and adapted to slow polarons emitted by the plasmon to thermal electrons; and
   a collector layer joined to the interface layer opposite from the top layer and adapted to collect the thermal electrons from the interface layer.

2. The detector of claim 1, wherein the interface layer comprises a substantially non-conductive π region.

3. The detector of claim 2, wherein the interface layer comprises any one or more of the group consisting of ZnSe, GaP, GaAs, and Si.

4. The detector of claim 1, wherein the collector layer comprises a semiconductor.

5. The detector of claim 1, wherein the top layer comprises any one or more of the group consisting of Au and Ag.

6. The detector of claim 1, farther comprising: an electric circuit adapted to conduct
   thermal electrons collected in the collector layer to the top layer.

7. A plasmon detector, comprising:
   means for generating a plasmon in a metal;
   means for reducing the energy of electrons emitted by decay of the plasmon; and
   means for detecting the reduced energy electrons.

* * * * *